United States Patent
Cool et al.

(10) Patent No.: US 6,605,052 B1
(45) Date of Patent: Aug. 12, 2003

(54) CORSET

(75) Inventors: Jan Constant Cool, Pijnacker (NL); Gert Nijenbanning, Oldenzaal (NL); Eddy Schuurman, Nijverdal (NL); Albert Gerrit Veldhuizen, Eelde (NL)

(73) Assignee: Orthodynamics B.V., Drachten (NL)

( * ) Notice: Subject to any disclaimer, the term of this patent is extended or adjusted under 35 U.S.C. 154(b) by 0 days.

(21) Appl. No.: 09/355,718

(22) PCT Filed: Feb. 2, 1998

(86) PCT No.: PCT/NL98/00066
§ 371 (c)(1),
(2), (4) Date: Nov. 16, 1999

(87) PCT Pub. No.: WO98/34570
PCT Pub. Date: Aug. 13, 1998

(30) Foreign Application Priority Data

Feb. 5, 1997 (NL) .............................................. 1005187

(51) Int. Cl.$^7$ .............................. A61F 5/00; A61F 5/24; A61F 5/28; A61F 5/26
(52) U.S. Cl. ...................... 602/19; 128/95.1; 128/102.1; 128/122.1
(58) Field of Search .......................... 602/5, 19, 23–25, 602/32, 36; 128/100.1, 99.1, 102.1, 103.1, 105.1, 869, 846, 95.1, 96.1, 101.1, 106.1, 112.1, 121.1, 122.1; 2/455–456, 44

(56) References Cited

U.S. PATENT DOCUMENTS

| | | | | |
|---|---|---|---|---|
| 148,718 A | * | 2/1874 | Lethert | |
| 954,005 A | * | 4/1910 | Roth | 602/19 |
| 1,595,739 A | * | 8/1926 | Stewart | 602/19 |
| 1,722,205 A | * | 7/1929 | Freund | |
| 1,793,776 A | * | 2/1931 | Clayton | 602/19 |
| 1,935,859 A | * | 11/1933 | Putz | |
| 2,453,370 A | * | 11/1948 | Hittenberger | 602/19 |
| 2,886,031 A | * | 5/1959 | Robbins | |
| 3,029,810 A | * | 4/1962 | Martin | |
| 3,351,053 A | * | 11/1967 | Stuttle | 602/19 |
| 3,548,817 A | * | 12/1970 | Mittasch | |
| 5,135,471 A | * | 8/1992 | Houswerth | 602/19 |
| 5,599,287 A | * | 2/1997 | Beczak et al. | |
| 5,782,783 A | * | 7/1998 | Young et al. | |

FOREIGN PATENT DOCUMENTS

DE 1640 * 3/1890

* cited by examiner

Primary Examiner—Denise M. Pothier
(74) Attorney, Agent, or Firm—Darby & Darby

(57) ABSTRACT

The invention relates to a corset for the treatment of a patient suffering from a back complaint, such as scoliosis, comprising a lower part to be supported by the hip, and an upper part to be fitted around the patient's chest. There is a flexible coupling provided to connect the lower part and the upper part. Both the lower part and the upper part are provided with an adjustable springy element to enable the lower part and the upper part to apply a pressure force on the patient's body.

10 Claims, 2 Drawing Sheets

CORSET

BACKGROUND OF THE INVENTION

1. Field of the Invention

The invention relates to a corset for the treatment of a patient suffering from a back complaint, such as scoliosis, comprising a lower part to be supported by the hip, and an upper part to be fitted around the patient's chest.

2. Description of the Related Art

The corset may be applied for various kinds of complaints, but for the sake of clarity it will be discussed in relation to scoliosis.

A corset of this kind is known, for instance, from the European patent application EP-A-0 234 372. The corset known from this publication is comprised of relatively rigid elements and forces the patient into a particular posture. In order to allow the patient some freedom of movement, a removable connecting element is provided between the lower part and the upper part. The known corset applies stationary pressure forces to the patient's body in order to stabilize and, if possible, to correct the scoliosis.

From DE-A-66,593 a corset is known comprising a lower part and an upper part which are interconnected in three places. The connecting elements comprise a band of spring steel, a steel element in the form of a horse shoe, and a pressure spring. The construction aims to provide the wearer of the corset with a permanent support and rotational pressure. However, the construction of this corset locks the patient into a rather tight straitjacket.

With regard to the working of the known corset, several theories exist which, briefly, amount to the following. In a first theory the body of the patient is stimulated to withdraw from the unpleasant feeling of the corset. To allow room for this, the known corset is provided with openings opposite to places where pressure is exerted on the patient's body. Another theory is that the corset produces an elastic deformation of the patient's body which with time will become a permanent correction.

Anyway, the known corset has a number of disadvantages obstructing effectiveness. As mentioned above, the known corset is rigid, resulting in poor wearing comfort. For this reason the known corset is usually only employed with the more serious forms of scoliosis. It is precisely these more serious forms of scoliosis that are less suitable for correction by means of a corset. The best result to be achieved with the known corset in such a case is stabilization of the scoliosis. Therefore, a need exists for a corset which is more comfortable in wear so that it invites usage even with lighter forms of scoliosis, whereby wearing the corset can become more effective.

A further disadvantage of the known corset is that because of the construction being so rigid, the patient runs the risk of hanging in the corset. The muscles are used less, especially since for the corset to be effective it must be worn at least 23 hours a day. The consequential weakening of the muscles is counterproductive with respect to the use of the known corset, in the sense that this may result in the worsening of the scoliosis. Yet another disadvantage of the known corset is that due to the rigid construction the corrective forces decrease, as the scoliosis improves. This requires constant adjustment of the known corset if the scoliosis is to be treated fully.

Still another disadvantage of the known corset is that the lower part is fitted so closely and even clasping the pelvic region so tightly that it causes pain.

Still another disadvantage of the known corset construction is that it forces the patient into so unnatural a posture, that it becomes obvious to others, which from a psychological viewpoint has a negative influence on the willingness to start wearing a corset.

BRIEF SUMMARY OF INVENTION

The object of the invention is now to remove these disadvantages. To this end the corset according to the invention is characterized in that a flexible coupling is provided to connect the lower part and the upper part. This flexible coupling allows the patient to move relatively freely even when wearing the corset according to the invention, improving the wearing comfort with the result that the willingness to actually wear the corset is positively influenced. This takes away the objections to wearing the corset also with lighter forms of scoliosis, thus allowing optimal exploitation of the efficacy of the corset's corrective action.

In a further aspect of the invention the corset is equipped such that both the lower part and the upper part are provided with an adjustable springy element to enable the lower part and the upper part to apply a pressure force on the patient's body. The springy element may be an adjustable elastic band. This increases the efficacy and functionality of the corset because the forces the corset exerts on the patient's body are thus made independent of the extent of correction of scoliosis being realized at any given moment during wear of the corset. Especially this advantage of the corset according to the invention distinguishes it decisively from the known corset.

The corset according to the invention should then be executed such that the springy element of the lower part is provided at the point where the lower part rests on the patient's pelvis, and that at the height of the patient's lumbar region, the lower part further comprises a support plate coupled with the springy element, which support plate is preferably also a springy element.

As mentioned, the support plate is located at the height of the scoliotic complaint, in the lumbar region of the back. Due to its customary s-form, the scoliosis frequently spans the entire back. The scoliosis in the upper back often becomes visible through the development of a gibbus (deformation of the ribs). A kind of gibbus also often appears in the lumbar region, due to a slight protrusion of the bundle of muscles at the convex side of the scoliosis. A corrective force is applied to both gibbuses. Even in the cases where the lumbar region does not exhibit any scoliosis, it is still necessary to apply a force to prevent that, as a result of correction of the upper region, a new curve develops in the lumbar region. The force exerted on the lumbar region has to prevent this.

Further, it is desirable that the springy element of the upper part is provided at the height of the scoliosis to be corrected and at the same side as the springy element of the lower part.

To properly distribute the forces to be applied to the patient's body, the upper part should further be provided with a pressure plate under the patient's armpit at the side opposite the springy element of the upper part, which pressure plate during wear is located somewhat higher than said springy element.

Finally, the upper part must be provided with at least one pressure plate at the height of the patient's sternum.

A simple embodiment for the realization of the flexible coupling is the embodiment using a hinged coupling. A particularly advantageous embodiment is the one in which the flexible coupling comprises a bar-like part and a sleeve-like part, with the bar-like part being at least to some extent slidable in the sleeve-like part, and the bar-like part and the sleeve-like part being attached to the lower part and the upper part, without both being attached to the same part. This embodiment very simply allows the patient to move his chest in relation to the pelvis both lengthways and sideways. It also makes it possible to turn the thorax in relation to the lower part of the body. In a particularly effective manner said embodiment affords the patient a mobility and wearing comfort not much inferior to the situation in which the corset is not required. In addition it is desirable, that a flexible connection is provided, for instance a light chain, for coupling the upper part with the lower part to prevent the corset from falling apart when putting it on and taking it off.

In this respect the corset according to the invention is very effective if only one single coupling is provided at the height of the patient's side.

A relatively open and therefore easily wearable and inconspicuous embodiment of the corset is characterized in that both the lower part and the upper part are substantially formed by a brace which together with the springy element, can surround the patient's body.

With the corsets of the prior art the pressure plates are rigidly attached to the corset. In a further aspect of the corset according to the invention the pressure plates are joined with the brace by means of a ball and socket joint, whereby said pressure plates at the side facing the brace are provided with a bulge fitting into a hollowing in a hinge element being a part of or being attached to the brace. The bulge may be attached to each pressure plate as separate part, or may be integrated by means of a local deformation of the pressure plate. Each pressure plate is kept in place by means of an O-ring. The O-ring ensures that after being relieved of pressure, the pressure plate returns to its original position. The construction works as a restrictive ball and socket joint, so that the pressure plates follow the form of the patient. In this way the direction of the forces is always perpendicular to the skin. There are no shearing forces which could cause pain or even injuries. Furthermore, the construction is very flat to prevent the corset from being visible under the clothing.

Exclusive rights are also requested for the corset's separate lower part and upper part respectively; said separate parts may be very usefully applied for the correction of certain forms of scoliosis.

The corset according to the invention will now be explained in more detail with the aid of a single, non-limiting exemplary embodiment and with reference to the appended drawing in which:

DETAILED DESCRIPTION OF THE PREFERRED EMBODIMENT

Figure 1:
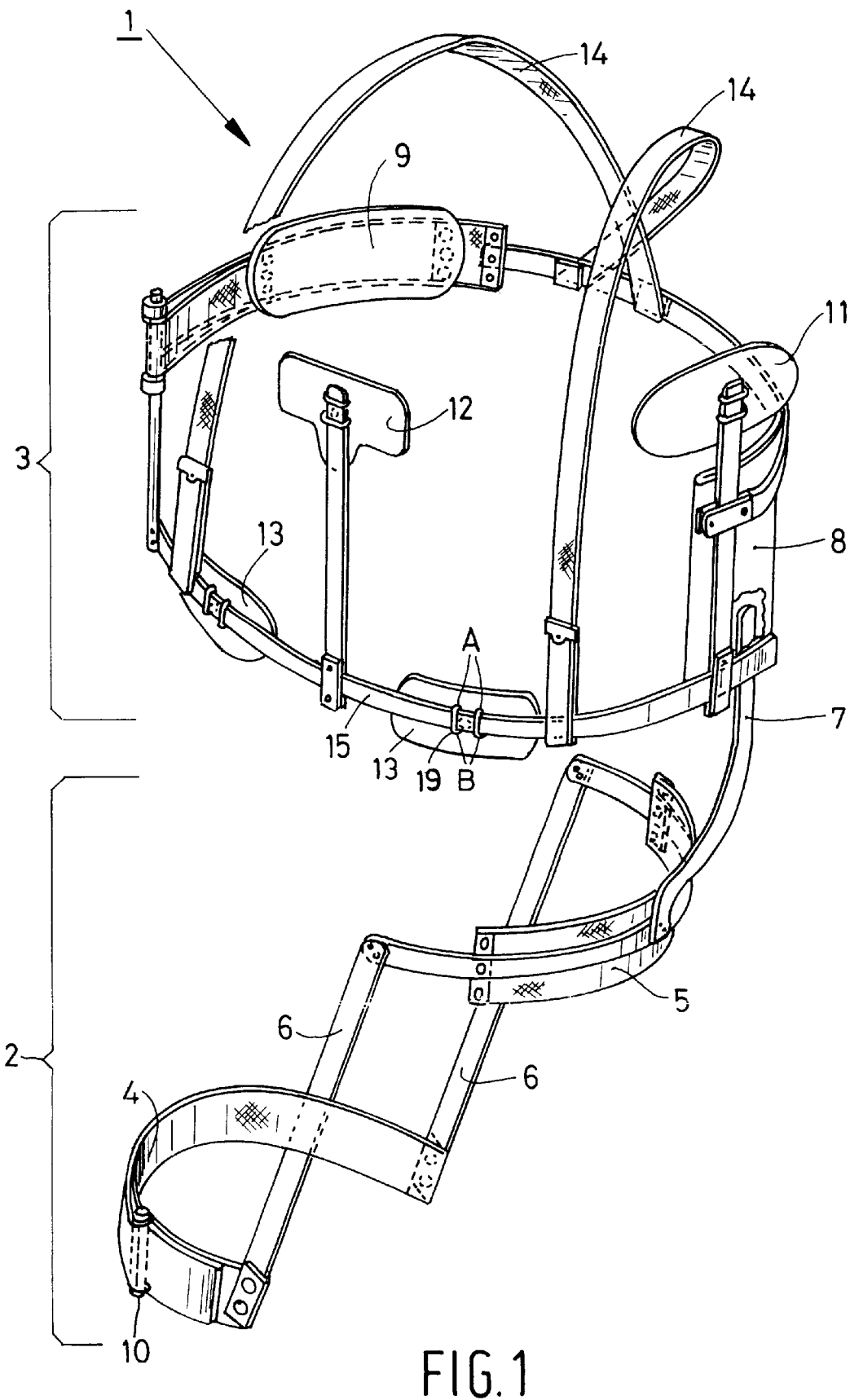
FIG. 1 shows the corset according to the invention.

FIG. 1 shows the corset, generally indicated by reference number 1, comprising a lower part 2 and an upper part 3. The lower part 2 is provided with a springy element 4 intended to be placed against the patient's pelvis, and with a support plate 5 which is connected to the springy element 4 by means of brace bars 6. The lower part is coupled to the upper part by means of a hinge coupling comprising a bar-like part 7 and a sleeve-like part 8. The Figure shows the embodiment such that the sleeve-like part 8 is coupled with the upper part 3, and the bar-like part 7 is coupled with the lower part 2. However, this configuration is interchangeable. The bar-like part is slidably inserted in the sleeve-like part 8 such as to allow the lower part 2 and the upper part 3 to move longitudinally in relation to each other, as well as allowing the upper part 3 to make a lateral movement and a rotational movement in relation to the lower part 2.

The upper part 3 is also provided with a springy element 9. Both the springy element 4 of the lower part 2 and the springy element 9 of the upper part 3 have elasticity and are provided with adjustment means. In the case shown, this is a VELCRO fastening, which is in itself known. With respect to the springy element 4 of the lower part 2, the adjustment is indicated by reference number 10. As illustrated, the springy element 9 of the upper part 3 is provided at the height of the gibbus to be corrected, in the upper part of the patient's back. The springy element 9 may be fitted with a support piece to prevent direct body contact with springy element 9, e.g., elastic band. Since it is believed that in addition to the lateral corrective movement of the respective section of the spinal column, the correction of a scoliosis also requires a rotational movement, the springy element 9 is placed such that the pressure force it exerts on the patient's back comes slightly oblique from the side. To complete the play of forces, the upper part 3 is further provided with a pressure plate 11 which is positioned opposite but higher than the springy element 9 of the upper part 3 at the patient's side under the arm pits. The upper part 3 finally is also provided with at least one pressure plate 12 at the height of the patient's sternum, as well as pressure plates 13 placed at the patient's front.

FIG. 1 clearly shows that both the lower part 2 and the upper part 3 are substantially formed by a brace, which together with the springy element 4 and 9 respectively can surround the patient's body. To prevent the corset from slipping down it may be provided with shoulder straps 14. The lower part and the upper part are coupled by means of a light chain (not shown) so as to keep them together when putting the corset on and taking it off.

Figure 2:
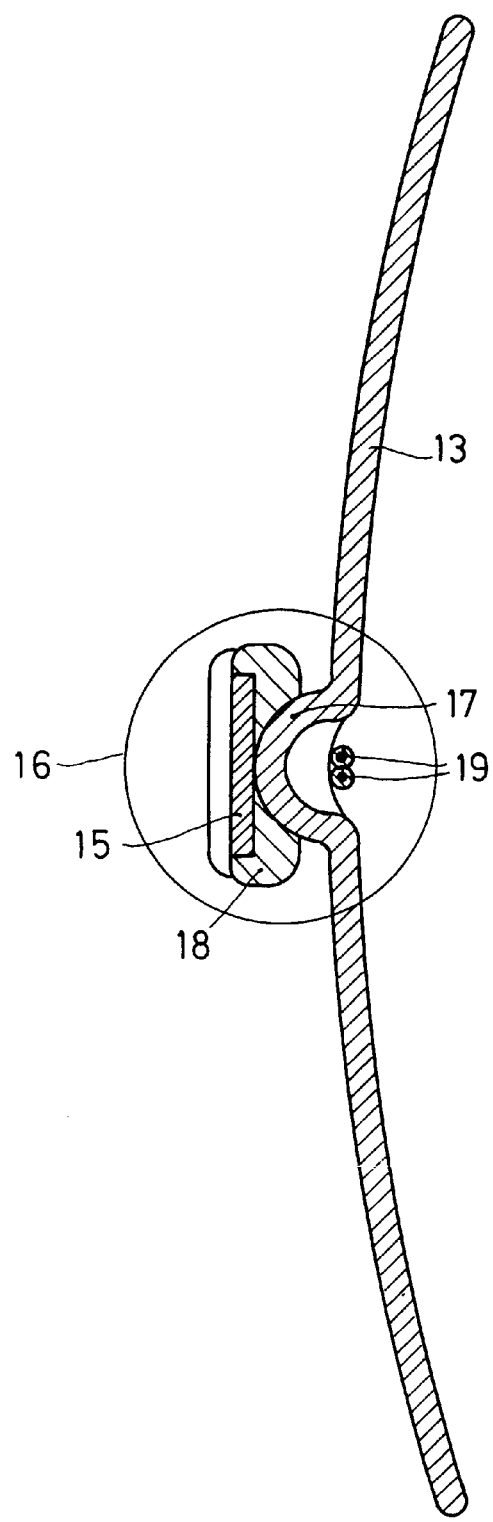
FIG. 2 shows a detailed view of the attachment of a pressure plate to the brace of the corset according to the invention.

FIG. 2 is a cross-sectional view of the attachment of a pressure plate 13 to the brace 15. Said attachment is effectuated by means of a ball and socket joint 16 which in the case illustrated, is formed by a bulge 17 being an integral part of the pressure plate, and bulging out away from the side intended to fit against the patient. This bulge 17 may also be a separate element attached to the pressure plate; in both embodiments said bulge fits into a corresponding hollowing of a hinge element 18 placed on the brace and attached thereto by means of, for instance, gluing. Further an O-ring 19 is applied, by means of which the pressure plate 13 is pulled against the brace 15. To this end the O-ring 19 is drawn through the holes A and B (FIG. 1) in the pressure plate 13. In the embodiment where the bulge is part of the pressure plate, the O-ring is positioned in the hollowing at the side of the pressure plate intended to fit against the patient.

It will be understood by the person skilled in the art that the embodiment discussed above is one of many possible embodiments, and that many variations are possible on this embodiment, which are all deemed to be within the scope of the appended claims.

What is claimed is:

1. A corset for treatment of a patient suffering from scoliosis, comprising:

a lower part to be supported by the hip and positioned to exert a corrective force in a lateral direction on the lumbar gibbus of the scoliosis;

an upper part to be fitted around the patient's chest and positioned to exert a corrective force in a lateral direction on the thoracal gibbus of the scoliosis;

a coupling which is provided to connect the lower part and the upper part, said coupling comprising a bar attached to one of the lower and upper parts, and a sleeve attached to the other of said parts, the bar being slidable in the sleeve; and wherein the coupling moves the upper part longitudinally, laterally and rotationally with respect to the lower part;

the lower part and the upper part are each provided with an adjustable springy element to enable the lower part and the upper part to apply a pressure force on the patient's body;

the springy element of the lower part is provided where the lower part is adapted to rest on the patient's pelvis; and the lower part further comprises a support plate coupled with the springy element adapted to rest on the patient's lumbar region at the side opposite and higher than the springy element of the lower part.

2. A corset according to claim 1, wherein the springy element of the upper part is adapted to rest on the patient's body at the height of the scoliosis to be corrected and at the same side of the patient as the springy element of the lower part.

3. A corset according to claim 2, wherein the upper part is provided with a pressure plate which is adapted to be placed under the patient's armpit at the side opposite but higher than the springy element of the upper part.

4. A corset according to claim 3, wherein the upper part is provided with at least one pressure plate adapted to be placed at the height of the patient's sternum.

5. A corset according to claim 1, wherein the coupling is adapted to be placed at the height just above the patient's hip.

6. A corset according to claim 5, wherein the upper part further includes a brace and wherein both the lower part and the upper part including the brace and the springy elements are adapted to substantially surround the patient's body.

7. A corset for the treatment of a patient suffering from a back complaint, comprising:

a lower part to be supported by the hip, having an adjustable springy element coupled with a support plate;

an upper part to be fitted around the patient's chest, having an adjustable springy element adapted to rest on the patient's body at the height of the scoliosis to be corrected and at the same side of the patient as the springy element of the lower part, a pressure plate adapted to be placed under the patient's armpit at the side opposite but higher than the springy element of the upper part, at least one pressure plate adapted to be placed at the height of the patient's sternum, a brace, and at least one pressure plate is joined with the brace by means of a ball and socket joint, whereby said at least one pressure plate at the side facing the brace is provided with a bulge fitting into a hollowing in a hinge element being a part of or being attached to the brace; and a coupling to be placed at the height just above the patient's hip, said coupling having a bar attached to one of the lower and upper parts, and a sleeve attached to the other of said parts, wherein the bar is slidable in the sleeve such that said coupling is adapted to allow the upper part to move longitudinally, laterally and rotationally with respect to the lower part.

8. A corset according to claim 7, wherein the at least one pressure plate is adjustably positioned on the brace by using an O-ring which pulls the at least one pressure plate against the brace.

9. A corset according to claim 8, wherein the O-ring is partially positioned in the hollowing at the side of the at least one pressure, plate adapted to face the patient's side.

10. A corset according to claim 9, wherein the hollowing of the at least one pressure plate is positioned on the reverse side and opposite the bulge.

* * * * *